United States Patent [19]

Brickell et al.

[11] 4,164,220
[45] Aug. 14, 1979

[54] ELECTRONIC TEMPERATURE SENSORS

[75] Inventors: Christopher G. Brickell; Derek A. Hodson, both of Auckland, New Zealand

[73] Assignee: Fisher & Paykel Limited, New Zealand

[21] Appl. No.: 707,481

[22] Filed: Jul. 22, 1976

[30] Foreign Application Priority Data

Jul. 23, 1975 [NZ] New Zealand .................. 178193
Sep. 2, 1975 [NZ] New Zealand .................. 178557

[51] Int. Cl.² ........................................... A61M 15/00
[52] U.S. Cl. ............................... 128/185; 73/362 R
[58] Field of Search ........ 128/419 P, 419 PG, 419 PS, 128/419 R, 419 B, 419 C, 419 E, 419 R, 420, 421, 422, 423, 2 E, 2 P, 2 H, 2 R, 2 S, 185, 2.05 D, 2.05 E, 2.05 P, 2.05 R, 2.1 E, 2.1 R, 1 D; 73/204, 347, 348, 362 R, 362 SC

[56] References Cited

U.S. PATENT DOCUMENTS

| 3,359,974 | 12/1967 | Khalil | 128/2.05 F |
| 3,486,506 | 12/1969 | Auphan | 128/419 P |
| 3,690,325 | 9/1972 | Kenny | 128/419 P |
| 3,789,831 | 2/1974 | Kopaniky et al. | 128/2.05 F |
| 3,866,616 | 2/1975 | Purdy et al. | 128/419 P |
| 3,906,959 | 9/1975 | Cannon | 128/419 P |

FOREIGN PATENT DOCUMENTS

| 1245604 | 9/1971 | United Kingdom . | |
| 1274882 | 5/1972 | United Kingdom | 128/419 P |

Primary Examiner—William E. Kamm
Attorney, Agent, or Firm—Holman & Stern

[57] ABSTRACT

An electronic device comprises a casing having a temperature sensor mounted therein with insulated sensor-connecting wires of considerable length being exposed to the environment on an external surface of the casing which is covered over the wires with a thin metallic coating.

2 Claims, 3 Drawing Figures

ELECTRONIC TEMPERATURE SENSORS

BACKGROUND OF THE INVENTION

This invention relates to passivating devised particularly though not solely for use in passivating devices used in measuring; or controlling temperature e.g. in the flow of gases from a humidifer to a hospitalised patient using such a humidifer and for similar purposes.

Depending on the environment it may be necessary to shield or passivate a device e.g. a pace maker implanted in a human being to control his heart function or to passivate a thermometer used to monitor temperatures of a gas in the presence of molecular water vapour, e.g. used in the connecting tube between the patient and a humidifier where the water vapour is 100% RH air at 37° C. Various procedures for passivation have been proposed but none have been found to be really satisfactory. The normal process for passivation of a thermistor is by coating it with glass, but this is not satisfactory, since it is a high temperature process and the pre-selected characteristics of interchangeable thermistors may be altered by the process. An alternative coating often used is a thin epoxy layer which may not provide adequate protection to the device and for example epoxy is liable to degradation by body fluids when used for the passivation of a pacemaking device for heart control when embedded in a human being. Furthermore in some types of devices e.g. thermal sensing devices, including those which sense the temperature in the connecting tube above referred to, it is desirable to have a fast response requiring a small thermal mass of the sensor and low thermal resistance between the sensor and the environment. Any additional passivation according to present methods usually result in an increased time constant because of increase in thermal mass and a higher thermal resistance.

It is an object of the invention in one aspect to provide a simple low cost and effective device which will obviate or minimise the foregoing disadvantages in a simple yet effective manner or which will at least provide the public with a useful choice.

SUMMARY OF THE INVENTION

The invention provides a mounted electronic device comprising a casing, a temperature sensor within said casing, insulated connecting wires connected to said sensor, parts of which wires are of considerable length exposed externally of said casing to the environment, the temperature of which is to be sensed by said sensor, and a thin metallic coating over at least some outer surfaces of said casing and over said parts of said connecting wires exposed externally of said casing.

The invention also envisages a mounting for use in combination with a sensor or sensor assembly such as that described above whereby the sensor may be quickly, readily and interchangeably mounted in a fitting, for example, in the connecting tube between a humidifier and a patient.

Such mounting comprises a junction member including at least a spigot connection and an opposite socket connection so that the mounting may be fitted in a tube having corresponding socket and spigot connections and a further opening adapted to receive a device, the device receiving opening and a part of the device being arranged to have mounted therebetween a sealing member, for example an O ring so that when the device is in position the sealing device effects a seal with the device positioned in the space between said spigot and socket connections.

To those skilled in the art to which this invention relates, many changes in construction and widely differing embodiments and applications of the invention will suggest themselves without departing from the scope of the invention as defined in the appended claims. The disclosures and the description herein are purely illustrative and are not intended to be in any sense limiting.

BRIEF DESCRIPTION OF THE DRAWINGS

One preferred form of the invention and modifications thereof will now be described with reference to the accompanying drawings in which.

Figure 3:
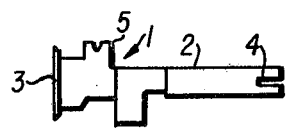
FIG. 3 is a side view to a different scale of a socket for the device of FIGS. 1 and 2.

Referring to the drawings, a mounting for a device such as a sensor or sensor assembly is provided as follows. A junction body 1 (FIG. 3) is provided having a spigot connection 2 and opposite this spigot connection 2 on the other side of the body is a socket connection 3 so that the mounting may be fitted in, for example, a tube 4 between a humidifier and a patient to whom gases are to be supplied from the humidifier. Preferably these spigot and socket members are tapered with a standard taper for a friction joint so that the mounting member may be quickly fixed in position and no further jointing made to the tube other than by use of the friction of the friction joints.

The junction 1 may be a T or X junction and one or both of the remaining outlets may be formed to receive a device which is to be mounted within the mounting member. Assuming a T junction, the mounting member is provided with a hollow cylinder 5 leading to the interior of the mounting member thus having substantially parallel sides although a small amount of "draw" will not affect the operation of the invention. A sensor mounting body 10 (FIGS. 1 and 2) to be mounted in the above fitting accordingly has a cylindrical part 11 with a groove 12 adapted to receive a sealing member, for example, an O ring 13 or the device otherwise is provided with a seal which will seal against the walls of the hollow cylindrical outlet of the mounting member.

The preferred form of the body provides a chamfer into the hollow cylindrical outlet of the mounting member so that the O ring 13 is compressed radially as the sensor is pushed into the mounting member. In the fitted position the O ring 13 passes across the full width of the chamfer and into a part of the hollow cylindrical member where the diameter is slightly greater and into which the O ring expands, although not sufficiently as to completely relax it which would prevent it sealing.

It will be appreciated that the pressure of the gas within the mounting member exerts a force on the sensor tending to push it out and it is necessary to have some form of restraint which is the purpose of the chamfer and retaining detail described. Before the sensor can be ejected the pressure must be such that the O ring is unseated from the increased diameter and pushed across the narrower portion and into the chamfered portion. The diameters are so arranged that this does not happen at normal respiratory pressures and so as to still enable the device to be easily removed and replaced by hand.

The advantages of this arrangement include both mechanical simplicity and simplicity of assembly, consistent positioning of the sensor in the mounting which cannot be achieved with a friction taper fitting and the combination of sealing and retention functions into one low cost component, allowing ease of replacement to contribute to the necessary high reliability of this sensor system.

Thus a series of devices may be provided each having the standardised cylindrical part of its body with a sealing member such that such devices are quickly and readily and easily interchanged within the mounting member. The advantages of this are considerable and the construction has particular advantages in the connecting tube of a humidifier as above referred to.

In particular the invention envisages a device which comprises a sensor, sensor assembly or other device for measuring temperature humidity or other conditions within the mounting member. Accordingly and referring in particular to a thermistor and mounting as a selected type of sensor according to the invention the thermistor 14 is passivated by first coating critical areas e.g. near connecting leads 15 and 16 of the thermistor with a thin insulating layer, for example, a urethane coating then preparing the coating by providing a conductive coating then for example by spraying or otherwise coating the insulating layer with a suitable conductive coating such as a conductive silver composition. This conductive coating is then increased in thickness by applying to the coating a metallic layer preferably by electroplating or electroforming a suitable metallic layer onto the coating. The insulating layer is provided to prevent the subsequent metallic plating from electrically joining any connecting wires or providing undesired contact with other parts of the assembly and accordingly after plating some cutting back or trimming of the coating may be necessary or alternatively parts of the insulating layer may be left out of the plating or forming bath to achieve a similar effect. Thus in FIG. 1 the metallic coating terminates at the base of wire supporting member 19 leaving the groove 12 and knob 17 uncoated.

By using a thin layer of insulating material the thermal conductivity of the sensor is not significantly affected and the addition of a suitable thickness of metal although slightly increasing the thermal mass, provides a larger low mass heat transfer area and rather than having a deleterious effect on the time constant may well in fact improve the time constant to give a faster responding system. A second advantage of the plating process if applied to the thermistor assembly and mounting frame is that a compatible coating is provided, this compatible coating being hard and metallic and may be chosen to provide resistance to the environment. The coating is easily cleaned by rubbing, brushing washing or any other suitable process and provides an easily sterilisable assembly.

Other types of sensors may be protected by the same process as described above and as stated the device has particular value where a sensor is used to monitor a gas in the presence of a molecular water vapour, for example 100% RH air at 37° C. where such a sensor or other device is used in, for example, the output tube of a humidifier as above referred to.

In order to support in particular a thermistor on a sensor body and to permit the metallic coating to be readily applied the illustrated sensor mounting body 10 is provided.

The body 10 has at one end the knob 17 whereby the body may be inserted and removed from the junction. The thermistor 14 is mounted in a cavity 18 in a terminal wire supporting member 19 comprising an oval or fish bellied shaped member having an oval width of for example, 12½ mm and a thickness of about ½ mm at each end and being thickened in the central portion by being on an arc of a circle of 20 mm radius between the ends. This oval member is provided with a series of slots 20 disposed between fins or ribs at the ends. One connecting wire 15 passes on one side of the oval member and the other wire 16 on the other side, the wires being then wrapped around the oval part and arranged in the slots so that the wires do not cross each other. The thermistor is then supported by the wires gripping the sides of the oval shaped member. The wires are then taken through appropriate apertures or slots away from, for example, the centre section of the knob through holes therein. This construction is then coated with an insulating layer as above described (or the wires only insulated) and after coating with a conductive coating treated as above described so that a metallic coating is provided over the thermistor in particular and over the insulated wires. The shaping of the oval part of the body is such so that the wires lie firmly on the surface when conformed to that surface with little risk of being separated from the surface resulting in, for example, an electroplated coating passing beneath the wire or between a wire and the body resulting perhaps in a short circuit or having other deleterious effects.

Figure 1:
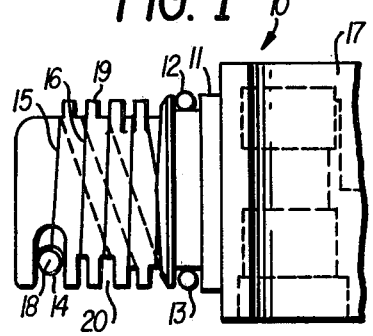
FIG. 1 is a side elevation of a passivated device according to the invention.
Figure 2:
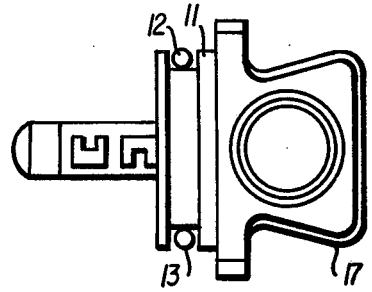
FIG. 2 is an end view of the device shown in FIG. 1.

In FIG. 1 the leads 15 and 16 are of considerable length and by exposing such long lengths of lead to the environment being sensed, namely the environment within the function and associated duties referred to above, the thermal gradient between the thermistor 14 and the external environment along the leads is such that the effect of changes in external temperatures have little effect on the thermistor.

Again, the thermal time constant of the thermistor 14 is not appreciably increased by the metallic coating so long as this coating is kept to practical thin thicknesses.

The sensor mounted on its body is then mounted in the junction as above described.

The above has been described in relation to a sensor and assembly. However it will be clear that the invention is applicable to other devices e.g. a "pace making" device for use by being implanted in the human body to control the functions of the heart of the patient and in such a device the device is insulated at least in the area of any connecting wires and is then coated in a similar manner as that above described. The metal applied to the device is one which is compatible with the host with which it is to be associated e.g. with the human body it is desirable that the device be coated with platinum or a similar metal which is not attacked by body fluids or by other fluids likely to be present in the parent body in which the device is used. In accordance with the above technique a first conductive layer is used to assist in electro forming or electro depositing a metal on the device or selected parts thereof which may be followed by other layers and, for example, copper, silver and platinum and any other combination of suitable metals are electro deposited or electroformed on the device. From the foregoing it will be seen that the invention is of general applicability and the precise type of device intended to be passivated is in no way limited.

In some circumstances it may be necessary to electroplate or electroform a layer of hard metal, e.g. chromium, followed by a passivating layer such as platinum so that there is adequate strength coupled with adequate passivation mutually compatible intervening layers e.g. silver, may be electroplated or electroformed in position.

Where the device comprises, for example, a pacing device for heart beats in a human patient, such device frequently uses an electrode with a glass to metal seal where the electrode passes through the wall of the device. non-reactive to the surrounding environment.

A metal member e.g. a ring of metal 26 and which surrounds the conductors 25 may be embedded in the glass to provide an anchor point for the enclosure 23 in an application where stress could cause loss of adhesion or bonding between the enclosure 23 and the glass 22 (or other material). The space 27 between the enclosure 23 and the object 21 may be packed with a filler. The filler may be an epoxy encapsulant, or if stress, e.g. due to thermal expansion could occur, the filler may be a compressible medium, e.g. a gas filled foam.

If batteries were included with the internal object 21 a gas space could be provided to allow for gas emission from the batteries.

The electrode style would depend on the intended application, and the plated surface could act as an electrode also.

The electroplating or electroforming used would depend on the nature of the surrounding environment.

FIG. 4 shows an enclosure 31 a part 32 of which is adhered directly to the seal material 33 and a different electrode arrangement. FIG. 5 shows a tortuous path 36 between the seal 37 and enclosure 38 to give better adhesion or peel strength or ingress path. The ring 26 could also have such a tortuous path.

In FIG. 6 an arrangement is shown using a commercial lead wire glassed in tube arrangement. Thus a lead wire 41 is mounted in glass disc 42 in turn mounted in a metal tube 43. A device 44, e.g. a pace maker is mounted in an infill 45 which may, for example, be capable of absorbing, for example, gases given off by a battery and a metallic coating 46 applied preferably but not necessarily including a part 47 adhered to the glass disc 42 but with clearance from the lead 41. The part 47 need not adhere with such tenacity to the glass 41a (FIG. 7) as to resist gas pressure but may be required to resist the ingress of fluids from the external environment onto the metal tube 43. To assist this an undulating surface 48 (FIG. 7) may be provided to the glass ring 41a and accordingly to the metal coating 49.

In all cases the metallic coating provides a hermetic seal that is to say the metallic coating seals against ingress, egress or transfer of undesired fluids or molecular or other solids otherwise capable of entering the protected environment.

The expression "passivating" used in this specification and claims is meant that an object is rendered substantially inert to selected fluids. Of course, this also implies that the metallic coating is corrosion resistant.

The invention has the advantages:

1. the temperatures at which the electroforming or electroplating is effected are low enough as to have no materially deleterious effect on electronic devices being passivated.

2. compatibility with a host, e.g. a human being where a heart pacemaker is involved, is readily achieved.

3. hermetic sealing is also readily achieved.

We claim:

1. A mounted electronic device comprising a mounting body, a temperature sensor carried by said mounting body, insulated connecting wires connected to said sensor, parts of which wires are of considerable length mounted externally of said mounting body and a thin metallic coating over at least some outer surfaces of said mounting body and over said parts of said connecting wires exposed externally of said mounting body with said thin metallic coating in intimate contact with said insulated connective wires.

2. A mounted electronic device as claimed in claim 1 wherein said mounting body has an oval part and said parts of said connecting wires are wrapped around said oval part.

* * * * *